United States Patent
Cooper et al.

(10) Patent No.: US 10,973,743 B2
(45) Date of Patent: *Apr. 13, 2021

(54) SKIN CARE FORMULATIONS CONTAINING COPOLYMERS AND INORGANIC METAL OXIDE PARTICLES

(71) Applicant: Rohm and Haas Company, Philadelphia, PA (US)

(72) Inventors: Beth Cooper, Doylestown, PA (US); Kinjalbahen Joshi, Collegeville, PA (US); Fanwen Zeng, Audubon, PA (US)

(73) Assignee: Rohm and Haas Company, Philadelphia, PA (US)

( * ) Notice: Subject to any disclaimer, the term of this patent is extended or adjusted under 35 U.S.C. 154(b) by 17 days.

This patent is subject to a terminal disclaimer.

(21) Appl. No.: 15/535,743

(22) PCT Filed: Dec. 18, 2015

(86) PCT No.: PCT/US2015/066590
§ 371 (c)(1),
(2) Date: Jun. 14, 2017

(87) PCT Pub. No.: WO2016/106115
PCT Pub. Date: Jun. 30, 2016

(65) Prior Publication Data
US 2017/0367944 A1    Dec. 28, 2017

Related U.S. Application Data

(60) Provisional application No. 62/095,170, filed on Dec. 22, 2014.

(51) Int. Cl.
| | |
|---|---|
| *A61K 8/27* | (2006.01) |
| *A61K 8/29* | (2006.01) |
| *A61Q 17/04* | (2006.01) |
| *A61K 8/81* | (2006.01) |
| *A61K 8/02* | (2006.01) |
| *A61K 8/19* | (2006.01) |

(52) U.S. Cl.
CPC .............. *A61K 8/27* (2013.01); *A61K 8/0241* (2013.01); *A61K 8/19* (2013.01); *A61K 8/29* (2013.01); *A61K 8/8152* (2013.01); *A61Q 17/04* (2013.01); *A61K 2800/624* (2013.01); *A61K 2800/651* (2013.01)

(58) Field of Classification Search
CPC .......... A61K 8/27; A61K 8/19; A61K 8/0241; A61K 8/29; A61K 8/8152; A61K 2800/624; A61K 2800/651; A61Q 17/04
See application file for complete search history.

(56) References Cited

U.S. PATENT DOCUMENTS

| | | | |
|---|---|---|---|
| 6,384,104 B1 * | 5/2002 | Chang | A61K 8/0279 |
| | | | 424/59 |
| 6,576,051 B2 | 6/2003 | Bardman et al. | |
| 6,710,161 B2 | 3/2004 | Bardman et al. | |
| 7,081,488 B2 | 7/2006 | Bardman et al. | |
| 7,179,531 B2 | 2/2007 | Brown et al. | |
| 7,265,166 B2 | 9/2007 | Gebhard et al. | |
| 8,557,895 B2 | 10/2013 | Ferencz et al. | |
| 2004/0091444 A1 | 5/2004 | Loffler et al. | |
| 2006/0286048 A1 | 12/2006 | Morrison et al. | |
| 2014/0194533 A1 | 7/2014 | Hsu et al. | |

FOREIGN PATENT DOCUMENTS

| | | |
|---|---|---|
| EP | 0625541 A2 | 11/1994 |
| EP | 0761201 A1 | 3/1997 |
| EP | 1092421 A2 | 4/2001 |
| EP | 1888039 A2 | 2/2008 |
| JP | 2005126329 A * | 5/2005 |
| JP | 2005126329 A | 5/2005 |
| WO | 2014084657 A1 | 6/2014 |
| WO | 2014093412 A1 | 6/2014 |
| WO | 2014205000 A1 | 12/2014 |
| WO | 2015094334 A1 | 6/2015 |

OTHER PUBLICATIONS

Kim, Jin-Woong, et al. "Titanium dioxide/poly (methyl methacrylate) composite microspheres prepared by in situ suspension polymerization and their ability to protect against UV rays." Colloid and Polymer Science 280.6 (2002): 584-588.*

Tyner, K. M., et al. "The state of nano-sized titanium dioxide (TiO2) may affect sunscreen performance." International journal of cosmetic science 33.3 (2011): 234-244.*

* cited by examiner

*Primary Examiner* — Sue X Liu
*Assistant Examiner* — Daniel L Branson
(74) *Attorney, Agent, or Firm* — Edward L. Brant

(57) ABSTRACT

Provided are skin care compositions that are useful as SPF and UV absorption boosters in formulations containing inorganic metal oxides. The compositions comprise (a) 0.1 to 20 weight % inorganic metal oxide particles, based on the weight of the composition, (b) 0.1 to 15 weight % copolymer particles dispersed in an aqueous medium, wherein the copolymer particles comprise polymerized units derived from (i) 0.1 to 20 weight % of phosphorus acid monomers, and (ii) 80 to 99.9 weight % of comonomers, and (c) a dermatologically acceptable carrier. Also provided are methods of protecting skin from UVA and UVB damage comprising topically administering such compositions to the skin, and methods of boosting the SPF or UV absorption of a sunscreen composition containing inorganic metal oxide particles comprising including such copolymer particles in the composition.

17 Claims, No Drawings

SKIN CARE FORMULATIONS CONTAINING COPOLYMERS AND INORGANIC METAL OXIDE PARTICLES

FIELD OF THE INVENTION

This invention relates generally to copolymers that are useful in skin care formulations. The skin care formulations contain copolymer particles bearing phosphorus acid groups with inorganic metal oxide particles.

BACKGROUND

Skin care compositions contain a variety of additives that provide a wide array of benefits to the composition. Sunscreen compositions in particular contain additives that offer protection from ultraviolet ("UV") radiation, which can damage the skin. UV radiation can be classified as UVA (long wave; i.e., wavelengths of 320-400 nm) and UVB (short wave; i.e., wavelengths of 290 to 320 nm). The efficacy of sunscreen formulations is measured by its sun protection factor ("SPF"). Since both UVA and UVB forms of radiation are harmful, sunscreen formulations offer protection from both kinds of rays. Inorganic metal oxide particles, such as titanium dioxide and zinc oxide, provide absorption of UVA and UVB radiation and to this end are commonly incorporated into sunscreen formulations. Inorganic metal oxides, however, can cause negative aesthetic qualities such as poor sensorial feel and an undesirable white appearance, both of which may be due to agglomeration of particles and poor distribution on skin.

Durability of sunscreen formulations is another consideration that has been addressed in the art. For example, U.S. Pat. No. 6,384,104 discloses UV radiation absorbing compositions containing a latex for the purpose of maintaining storage stability of sunscreen formulations when added to personal care compositions. The prior art does not, however, disclose a formulation containing inorganic metal oxide particles and copolymer particles according to the present invention which gives superior results as a UV absorption booster.

Accordingly, there is a need to develop new sunscreen compositions including sunscreen boosters which will help provide a high SPF, while improving aesthetic qualities of such formulations such as sensorial feel and visual appearance.

STATEMENT OF INVENTION

One aspect of the invention provides a skin care composition comprising (a) 0.1 to 20 weight % inorganic metal oxide particles, based on the weight of the composition, (b) 0.1 to 15 weight % copolymer particles dispersed in an aqueous medium, based on the weight of the composition, wherein the copolymer particles comprise polymerized units derived from (i) 0.1 to 20 weight % of phosphorus acid monomers, and (ii) 80 to 99.9 weight % of comonomers, and (c) a dermatologically acceptable carrier.

In another aspect, the invention provides a method for protecting skin from UVA and UVB damage comprising topically administering to the skin a sunscreen composition comprising (a) 0.1 to 20 weight % inorganic metal oxide particles, based on the weight of the composition, (b) 0.1 to 15 weight % copolymer particles dispersed in an aqueous medium, based on the weight of the composition, wherein the copolymer particles comprise polymerized units derived from (i) 0.1 to 20 weight % of phosphorus acid monomers, and (ii) 80 to 99.9 weight % of comonomers, and (c) a dermatologically acceptable carrier.

Another aspect of the invention provides a method of boosting the SPF or UV absorption of a sunscreen composition containing inorganic metal oxide particles comprising including copolymer particles dispersed in an aqueous medium, wherein the copolymer particles comprise polymerized units derived from (i) 0.1 to 20 weight % of phosphorus acid monomers, and (ii) 80 to 99.9 weight % of comonomers.

DETAILED DESCRIPTION

The inventors have now surprisingly found copolymer particles comprising polymerized units derived from phosphorus acid monomers provide a boost in SPF or UV absorption in sunscreen formulations containing inorganic metal oxides, while also improving the aesthetic qualities, e.g., sensorial feel and visual appearance, of such formulations when applied to the skin. Accordingly, the present invention provides in one aspect a skin care composition comprising inorganic metal oxide particles, copolymer particles dispersed in an aqueous medium comprising polymerized units of phosphorus acid monomers and comonomers, and a dermatologically acceptable carrier.

In the present invention, "skin care compositions" is intended to refer to compositions for leave on application to the skin, such as lotions, creams, gels, gel creams, serums, toners, wipes, liquid foundations, make-ups, tinted moisturizer, oils, face/body sprays, topical medicines, and sunscreen compositions. "Sunscreen compositions" refers to compositions that protect the skin from UV damage. Preferably, the skin care composition is cosmetically acceptable. "Cosmetically acceptable" refers to ingredients typically used in personal care compositions, and is intended to underscore that materials that are toxic when present in the amounts typically found in personal care compositions are not contemplated as part of the present invention. The compositions of the invention may be manufactured by processes well known in the art, for example, by means of conventional mixing, dissolving, granulating, emulsifying, encapsulating, entrapping or lyophilizing processes.

As used herein, the term "polymer" refers to a polymeric compound prepared by polymerizing monomers, whether of the same or a different type. The generic term "polymer" includes the terms "homopolymer," "copolymer," and "terpolymer." As used herein, the term "polymerized units derived from" refers to polymer molecules that are synthesized according to polymerization techniques wherein a product polymer contains "polymerized units derived from" the constituent monomers which are the starting materials for the polymerization reactions.

As used herein, the term "(meth)acrylate" refers to either acrylate or methacrylate, and the term "(meth)acrylic" refers to either acrylic or methacrylic.

As used herein, the term "phosphorus acid group" refers to a phosphorus oxo acid having a POH moiety in which the hydrogen atom is ionizable. Also included in the term "phosphorus acid group" are salts of the phosphorus oxo acid. In its salt or basic form, the phosphorus acid group has a cation such as a metal ion or an ammonium ion replacing at least one acid proton. Examples of phosphorus acid groups include groups formed from phosphinic acid, phosphonic acid, phosphoric acid, pyrophosphinic acid, pyrophosphoric acid, partial esters thereof, and salts thereof.

As used herein, the terms "glass transition temperature" or "$T_g$," refers to the temperature at or above which a glassy polymer will undergo segmental motion of the polymer chain. Glass transition temperatures of a polymer can be estimated by the Fox equation (*Bulletin of the American Physical Society*, 1 (3) Page 123 (1956)) as follows:

$$1/T_g = w_1/T_{g(1)} + w_2/T_{g(2)}$$

For a copolymer, $w_1$ and $w_2$ refer to the weight fraction of the two comonomers, and $T_{g(1)}$ and $T_{g(2)}$ refer to the glass transition temperatures of the two corresponding homopolymers made from the monomers. For polymers containing three or more monomers, additional terms are added ($w_n/T_{g(n)}$). The $T_{(g)}$ of a polymer can also be calculated by using appropriate values for the glass transition temperatures of homopolymers, which may be found, for example, in "Polymer Handbook," edited by J. Brandrup and E. H. Immergut, Interscience Publishers. The $T_g$ of a polymer can also be measured by various techniques, including, for example, differential scanning calorimetry ("DSC"). The values of $T_g$ reported herein are measured by DSC.

The inventive skin care compositions contain inorganic metal oxide particles. Suitable inorganic metal oxides include, for example, zinc oxide (ZnO), titanium dioxide (TiO$_2$), and mixtures thereof. In certain embodiments, the inorganic metal oxide particles are pigment grade ZnO or pigment grade TiO$_2$. In certain embodiments, the inorganic metal oxide particles are transparent ZnO or transparent TiO$_2$. Most inorganic metal oxides used in sunscreen formulations produce a cosmetically undesirable white appearance caused by light scattering. Thus, as used herein, the term "transparent" inorganic metal oxide sunscreen particle refers to inorganic metal oxide particles produced by a variety of processing conditions which render compositions containing such particles as clear, or more transparent than pigment grade, upon application. Suitable ZnO particles include, for example, those commercially available under the trade names Z-COTE from BASF Corporation, ZIN-CLEAR IM from Antaria Limited, and Z-CLEAR from Actifirm. Suitable TiO$_2$ particles include, for example, those commercially available under the trade names TIPAQUE and TTO-51(A) from Ishiharra Sangyo Kaisha, Ltd., T-COTE from BASF Corporation, UFTR (from Miyoshi Kasei), and SOLAVEIL CLARUS from Uniquema. In certain embodiments, the skin care compositions include inorganic metal oxide particles in an amount of from 0.1 to 20 weight %, preferably from 0.5 to 18 weight %, and more preferably from 1 to 15 weight %, by weight of the composition.

The skin care compositions of the present invention also contain copolymer particles bearing phosphorus acid groups pendant to the polymer backbone. These phosphorus acid groups are referred to herein as "first phosphorus acid groups." The copolymer particles are dispersed in an aqueous medium, and are insoluble in the aqueous medium. The copolymer particles are addition polymers, which comprise polymerized units derived from (i) ethylenically unsaturated monomers having a phosphorus acid groups, referred to herein as "phosphorus acid monomers," and (ii) ethylenically unsaturated monomers, referred to herein as "comonomers."

The phosphorus acid monomers contain at least one ethylenic unsaturation and a phosphorus acid group. The phosphorus acid monomer may be in the acid form or as a salt of the phosphorus acid group. Suitable phosphorus acid monomers include, for example:

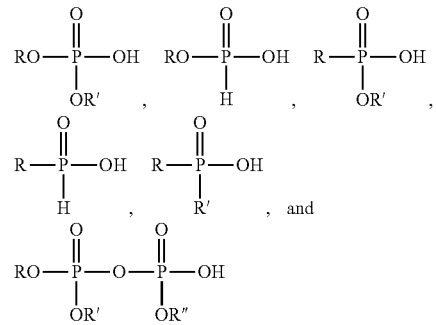

wherein R is an organic group containing an acryloxy, methacryloxy, or a vinyl group; and R' and R" are independently selected from H and a second organic group. The second organic group may be saturated or unsaturated. Suitable phosphorus acid monomers include, for example, dihydrogen phosphate-functional monomers, e.g., dihydrogen phosphate esters of an alcohol in which the alcohol also contains a polymerizable vinyl or olefinic group (e.g., allyl phosphate, mono- or diphosphate of bis(hydroxyl-methyl) fumarate or itaconate), and derivatives of (meth)acrylic acid esters, e.g., phosphates of hydroxyalkyl (meth)acrylates (e.g., 2-hydroxyethyl (meth)acrylate and 3-hydroxypropyl (meth)acrylates). Other suitable phosphorus acid monomers include, for example phosphonate functional monomers, e.g., vinyl phosphonic acid, allyl phosphonic acid, α-phosphonostyrene, and 2-methylacrylamido-2-methyl-propanephosphonic acid. Further suitable phosphorus functional monomers include, for example, 1,2-ethylenically unsaturated (hydroxy)phosphinylalkyl (meth)acrylate monomers, e.g., (hydroxy)phosphinylmethyl methacrylate. In certain preferred embodiments, the phosphorus acid monomers comprise dihydrogen phosphate monomers, e.g., 2-phosphoethyl (meth)acrylate, 2-phosphopropyl (meth)acrylate, 3-phosphopropyl (meth)acrylate, and 3-phospho-2-hydroxypropyl (meth)acrylate. In certain embodiments, the inventive copolymers comprise polymerized units of phosphorus acid monomers in an amount of at least 0.1 weight %, preferably at least 0.5 weight %, and more preferably at least 1 weight %, by weight of the copolymer. In certain embodiments, the inventive copolymer comprise polymerized units of phosphorus acid monomers in an amount of no more than 20 weight %, preferably no more than 10 weight %, and more preferably no more than 6 weight %.

The comonomers are ethylenically unsaturated monomers which are not phosphorus acid monomers and are copolymerizable with an ethylenically unsaturated phosphorus acid monomer. Suitable comonomers include, for example, styrene, butadiene, α-methyl styrene, vinyl toluene, vinyl naphthalene, ethylene, propylene, vinyl acetate, vinyl versatate, vinyl chloride, vinylidene chloride, acrylonitrile, methacrylonitrile, (meth)acrylamide, various $C_1$-$C_{40}$ alkyl esters of (meth)acrylic acid (e.g., methyl (meth)acrylate, ethyl (meth)acrylate, n-butyl (meth)acrylate, 2-ethylhexyl (meth)acrylate, cyclohexyl (meth)acrylate, n-octyl (meth)acrylate, n-decyl (meth)acrylate, n-dodecyl (meth)acrylate, tetradecyl (meth)acrylate, lauryl (meth)acrylate, oleyl (meth)acrylate, palmityl (meth)acrylate, and stearyl (meth)acrylate)), and other (meth)acrylates (e.g., isobornyl (meth)acrylate, benzyl (meth)acrylate, phenyl (meth)acrylate, 2-bromoethyl (meth) acrylate, 2-phenylethyl (meth)acrylate, and 1-naphthyl (meth)acrylate)), alkoxyalkyl (meth)acrylates, e.g., ethoxyethyl (meth)acrylate, mono-, di-, trialkyl esters of ethylenically unsaturated di- and tricarboxylic acids and anhydrides (e.g., ethyl maleate, dimethyl fumarate, trimethyl aconitate, and ethyl methyl itaconate), and carboxylic acid containing monomers, e.g., (meth)acrylic acid, itaconic acid, fumaric acid, and maleic acid. In certain embodiments, the inventive copolymers comprise polymerized units of comonomers in an amount of at least 80 weight %, preferably at least 90 weight %, and more preferably at least 94 weight %, by weight of the copolymer. In certain embodiments, the inventive copolymer comprise polymerized units of comonomers in an amount of no more than 99.9 weight %, preferably no more than 99.5 weight %, and more preferably no more than 99 weight %.

In certain embodiments, the polymer may be a crosslinked polymer, wherein a crosslinker, such as a monomer having two or more non-conjugated ethylenically unsaturated groups, is included with the copolymer components during polymerization. Suitable crosslinker monomers include, for example, di- or tri-allyl ethers and di- or tri-(meth)acrylyl esters of diols or polyols (e.g., trimethylolpropane diallyl ether, ethylene glycol dimethacrylate), di- or tri-allyl esters of di- or tri-acids, allyl (meth)acrylate, divinyl sulfone, triallyl phosphate, divinylaromatics (e.g., divinylbenzene). In certain embodiments, the inventive copolymers comprise polymerized units of crosslinker monomers in an amount of no more than 5 weight %, preferably no more than 3 weight %, more preferably no more than 2 weight %, and even more preferably no more than 1 weight %, by weight of the copolymer.

Polymer molecular weights can be measured by standard methods such as, for example, size exclusion chromatography or intrinsic viscosity. In certain embodiments, the copolymer particles of the present invention have a weight average molecular weight ($M_w$) of 5,000,000 or less, preferably 3,000,000 or less, more preferably 2,000,000 or less, and even more preferably 1,000,000 or less, as measured by gel permeation chromatography. In certain embodiments, the copolymer particles have a $M_w$ of 5,000 or more, preferably 50,000 or more, and more preferably 100,000 or more, as measured by gel permeation chromatography. Copolymer particles suitable for use in the inventive skin care compositions have $T_g$ values in the range of from 25° C. to 150° C., preferably from 50° C. to 150° C., and more preferably from 60° C. to 100° C. In certain embodiments, the inventive copolymer particles have an average diameter in a range of from 10 nm to 20 microns, preferably from 20 nm to 1 micron, and more preferably from 50 nm to 500 nm. The diameters of the copolymer particles may be characterized by distributions such as unimodal or multimodal, including bimodal. The average diameter of the copolymer particles may be determined by a light scattering technique.

In certain embodiments, the inventive skin care composition includes copolymer particles in an amount of from 0.1 to 15 weight %, preferably from 0.5 to 10 weight %, and more preferably from 1 to 8 weight, by weight of the composition. In certain embodiments, the skin care composition includes the inorganic metal oxide and copolymer particles in a weight ratio of from 2:8 to 8:2, preferably from 3:7 to 7:3, and more preferably from 4:6 to 6:4.

Suitable polymerization techniques for preparing the copolymer particles contained in the inventive skin care compositions include, for example, emulsion polymerization and solution polymerization, preferably emulsion polymerization, as disclosed in U.S. Pat. No. 6,710,161. Aqueous emulsion polymerization processes typically are conducted in an aqueous reaction mixture, which contains at least one monomer and various synthesis adjuvants, such as the free radical sources, buffers, and reductants in an aqueous reaction medium. In certain embodiments, a chain transfer agent may be used to limit molecular weight. The aqueous reaction medium is the continuous fluid phase of the aqueous reaction mixture and contains more than 50 weight % water and optionally one or more water miscible solvents, based on the weight of the aqueous reaction medium. Suitable water miscible solvents include, for example, methanol, ethanol, propanol, acetone, ethylene glycol ethyl ethers, propylene glycol propyl ethers, and diacetone alcohol. In certain embodiments, the aqueous reaction medium contains more than 90 weight % water, preferably more than 95 weight % water, and more preferably more than 98 weight % water, based on the weight of the aqueous reaction medium. In certain embodiments, the aqueous reaction medium has a pH of less than or equal to 8, and preferably having a pH of less than or equal to 4.

The polymerization process may be conducted as a batch, semicontinuous, or continuous process. In certain embodiments, the polymer is formed in a two stage reaction. In certain embodiments, the first stage comprises polymerizing 1 to 10 weight % of phosphorus acid monomers, 99 to 80 weight % comonomers, and 0 to 5 weight % of crosslinker, based on the total weight of monomers polymerized in the first stage. In certain embodiments, the second stage comprises polymerizing 95 to 100 weight % comonomers, and 0 to 5 weight % of crosslinker, based on the total weight of monomers polymerized in the second stage. In certain embodiments, the phosphorus acid monomers comprise a phosphoethyl methacrylate. In certain embodiments, the comonomers comprise at least one of butyl acrylate, methyl methacrylate, and methacrylic acid. In certain embodiments, the crosslinker comprises allyl methacrylate. In certain embodiments, the total ratio of monomers polymerized in stage 1 and stage 2 ranges from 20:80 to 80:20, preferably from 25:75 to 75:25, and more preferably from 30:70 to 70:30.

The inventive skin care compositions contain the copolymer particles dispersed in an aqueous medium. The aqueous medium may contain cosolvents, e.g., water miscible cosolvents. Suitable water miscible cosolvents include, for example, methanol, ethanol, propanol, acetone, ethylene glycol ethyl ethers, propylene glycol propyl ethers, and diacetone alcohol; and water immiscible solvents such as propyl acetate, butyl acetate, methyl isoamyl ketone, amyl acetate, diisobutyl ketone, xylene, toluene, butanol, and mineral spirits. The pH of the skin care composition may be in the range of 3 to 11.

In certain embodiments, the skin care composition is characterized as being substantially-free of water soluble phosphorus acid compounds. Water soluble phosphorus acid compounds contain phosphorus acid groups, referred to herein as "second phosphorus acid groups." At a pH of 5 and above, the water soluble phosphorus acid compounds are contained as a solubilized component of the aqueous medium. The water soluble phosphorus acid compounds include inorganic phosphorus acid compounds and organic phosphorus acid compounds. Inorganic phosphorus acid compounds include phosphorus oxo acids such as phosphoric acid, phosphorus acid, hydrophosphorous acid, orthophosphoric acid, pyrophosphoric acid, and salts thereof. Organic phosphorus acid compounds contain at least one phosphorus acid group attached to an organic moiety and include both unsaturated organic phosphorus acid compounds such as phosphorus acid monomers; and saturated organic phosphorus oxo acids such as partial esters of phosphorus oxo acids such as $HOCH_2CH_2OP(O)(OH)_2$, methyl phosphonic acid, and water soluble polymer bearing phosphorus acid groups. The water soluble polymer bearing phosphorus acid groups are addition polymers containing at least two phosphorus acid groups that are independently located pendant to the backbone of the water soluble polymer or in a terminal position. The water soluble polymer bearing phosphorus acid groups may be a homopolymer or a copolymer, and has a degree of polymerization of at least 2. As used herein, "saturated phosphorus acid compounds" are compounds selected from inorganic phosphorus acid compounds and saturated organic phosphorus acid compounds. As used herein, "substantially-free of water soluble phosphorus acid compounds" refers to a level of water soluble phosphorus acid compounds in the polymer composition as defined by the ratio of equivalents of second phosphorus acid groups to equivalents of first phosphorus acid groups in a range having an upper value of 0.8, preferably 0.7, and more preferably 0.5; and may have a lower value in the range of 0.1, preferably 0.05, and more preferably zero. In one embodiment, the ratio of equivalents of second phosphorus acid groups to equivalents of first phosphorus acid groups is in the range of less than or equal to 0.8, preferably less than or equal to 0.7, and more preferably less than or equal to 0.5. The ratio of equivalents of second phosphorus acid groups to equivalents of first phosphorus acid groups in the skin care composition is determined by inductively coupled plasma spectroscopy detection of phosphorus atoms, as disclosed in U.S. Pat. No. 6,710,161. The first phosphorus acid groups and the second phosphorus acid groups may be the same type of phosphorus acid or may be different; for example, the first phosphorus acid groups may be formed from phosphoric acid and the second phosphorus acid groups may be formed from phosphonic acid.

In certain embodiments of the present invention, the inventive skin care composition comprises a composite particle composition wherein the copolymer particles are adsorbed onto the surface of the inorganic metal oxide particles to form composite particles. While not wishing to be bound by theory, it is believed that the contact between adjacent inorganic metal oxide particles is minimized due to the adsorption of copolymer particles onto the surface of each inorganic metal oxide particle. The copolymer particles may fully cover the surface of the inorganic metal oxide particle to provide an encapsulating layer or may partially cover the inorganic metal oxide particle surface. The composite particles are useful for providing sunscreen agents with improved absorbance of UV radiation and increased SPF performance compared to compositions containing equivalent levels of unaltered inorganic metal oxide particles (i.e., not containing composite particles).

The composite particles may include copolymer particles with a single polymer phase or two-phase copolymer particles that have the phosphorus acid groups in one or more phases in contact with the exterior of the copolymer particle. In one embodiment, the composite particle contains two-phase copolymer particles having one polymer phase that does not completely encapsulate the second polymer phase.

In certain embodiments, the composite particles contain copolymer particles having an average particle diameter in the range of 40 nm to 50 µm, preferably in the range of 50 nm to 5 µm, and more preferably in the range of 60 nm to 1 µm. In certain embodiments, the composite particles contain copolymer particles having $T_g$ values in the range of from 25° C. to 150° C., preferably from 50° C. to 150° C., and more preferably from 60° C. to 100° C. In certain embodiments, the pH of the inventive skin care compositions containing the composite particles may be in the range of from 3 to 10, and preferably a pH of from 7 to 9.

Inventive skin care compositions including the composite particles containing the copolymer particles may be prepared by first admixing a first aqueous medium containing a dispersion of inorganic metal oxide particles, and a copolymer composition containing the copolymer particles. The copolymer particles are allowed sufficient time to adsorb to the inorganic metal oxide particles to form the composite particles. The adsorption of the copolymer particles to the inorganic metal oxide particles is believed to be spontaneous and will continue until the copolymer particles are completely adsorbed to the surfaces of the inorganic metal oxide particles, the surfaces of the inorganic metal oxide particles are completely covered with copolymer particles, or until an equilibrium is achieved between adsorbed copolymer particles and copolymer particles remaining dispersed in the aqueous medium of the composite particle composition.

Skin care compositions of the invention also include a dermatologically acceptable carrier. Such material is typically characterized as a carrier or a diluent that does not cause significant irritation to the skin and does not negate the activity and properties of active agent(s) in the composition. Examples of dermatologically acceptable carriers that are useful in the invention include, without limitation, water, such as deionized or distilled water, emulsions, such as oil-in-water or water-in-oil emulsions, alcohols, such as ethanol, isopropanol or the like, glycols, such as propylene glycol, glycerin or the like, creams, aqueous solutions, oils, ointments, pastes, gels, lotions, milks, foams, suspensions, powders, or mixtures thereof. In some embodiments, the composition contains from about 99.99 to about 50 percent by weight of the dermatologically acceptable carrier, based on the total weight of the composition.

The skin care compositions of the invention may also include sunscreen actives in addition to the inorganic metal oxide particles. Suitable additional sunscreen actives include, for example, para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, titanium dioxide, zinc oxide, benzophenones, benzylidenes, salicylates, or other known UV filters, including diethanolamine methoxycinnamate, digalloy trioleate, ethyl dihydroxypropyl PAB A, glyceryl aminobenzoate, and lawsone with dihydroxy acetone and red petrolatum.

The skin care compositions of the invention may also include other ingredients known in the art of sunscreen formulations including, for example, a thickener, emollients, an emulsifier, a humectant, a surfactant, a suspending agent, a film forming agent, a lower monoalcoholic polyol, a high boiling point solvent, a propellant, a mineral oil, silicon feel modifiers, or mixtures thereof. The amount of optional ingredients effective for achieving the desired property provided by such ingredients can be readily determined by one skilled in the art.

Other additives may be included in the compositions of the invention such as, but not limited to, abrasives, absorbents, aesthetic components such as fragrances, pigments, colorings/colorants, essential oils, skin sensates, astringents (e.g., clove oil, menthol, camphor, eucalyptus oil, eugenol, menthyl lactate, witch hazel distillate), preservatives, anticaking agents, a foam building agent, antifoaming agents, antimicrobial agents (e.g., iodopropyl butylcarbamate), antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, propellants, reducing agents, sequestrants, skin bleaching and lightening agents (e.g., hydroquinone, kojic acid, ascorbic acid, magnesium ascorbyl phosphate, ascorbyl glucosamine), skin-conditioning agents (e.g., humectants, including miscellaneous and occlusive), skin soothing and/or healing agents (e.g., panthenol and derivatives (e.g., ethyl panthenol), aloe vera, pantothenic acid and its derivatives, allantoin, bisabolol, and dipotassium glycyrrhizinate), skin treating agents, and vitamins (e.g., Vitamin C) and derivatives thereof. The amount of option ingredients effective for achieving the desired property provided by such ingredients can be readily determined by one skilled in the art.

As noted above, skin care compositions of the present invention are highly effective as SPF and UV absorption boosters. Accordingly, the skin care compositions of the present invention are useful for the treatment and protection of skin, including, for example, protection from UV damage, moisturization of the skin, prevention and treatment of dry skin, protection of sensitive skin, improvement of skin tone and texture, masking imperfections, and inhibition of transepidermal water loss. Thus, in one aspect the present invention provides that the skin care compositions may be used in a method for protecting skin from UVA and UVB damage comprising topically administering to the skin a composition comprising (a) 0.1 to 20 weight % inorganic metal oxide particles, based on the weight of the composition, (b) 0.1 to 15 weight % copolymer particles as described herein dispersed in an aqueous medium, based on the weight of the composition, and (c) a dermatologically acceptable carrier. The compositions may also be used in a method for boosting the SPF or UV absorption of a sunscreen composition containing inorganic metal oxide particles comprising including in the composition copolymer particles as described herein in an aqueous medium. In certain embodiments, the inventive sunscreen compositions containing inorganic metal oxide particles and copolymers described herein have an SPF that is more than 25% higher, and preferably more than 50% higher, than compositions containing equivalent levels of unaltered inorganic metal oxide particles (i.e., not containing composite particles)

In practicing the methods of the invention, the skin care compositions are generally administered topically by applying or spreading the compositions onto the skin. A person of ordinary skill in the art can readily determine the frequency with which the compositions should be applied. The frequency may depend, for example, on the level of exposure to UV light that an individual is likely to encounter in a given day and/or the sensitivity of the individual to UV light. By way of non-limiting example, administration on a frequency of at least once per day may be desirable.

Some embodiments of the invention will now be described in detail in the following Examples.

EXAMPLES

Example 1

Preparation of Exemplary Copolymer Particles

Exemplary copolymer particles in accordance with the present invention contain the components recited in Table 1.

TABLE 1

Exemplary Copolymer Particles

| Sample | Monomer (wt %) |
|---|---|
| P1 | Stage 1 (35%): 11 BA/82.2 MMA/6.6 PEM/0.2 MAA |
| | Stage 2 (65%): 14.1 BA/85.7 MMA/0.2 MAA |
| P2 | Stage 1 (35%): 10.8 BA/81 MMA/8.0 PEM/0.2 MAA |
| | Stage 2 (65%): 14.1 BA/85.7 MMA/0.2 MAA |
| P3 | Stage 1 (35%): 11.2 BA/83.5 MMA/5.1 PEM/0.2 MAA |
| | Stage 2 (65%): 14.1 BA/85.7 MMA/0.2 MAA |
| P4 | Stage 1 (35%): 11.2 BA/83.5 MMA/5.1 PEM/0.2 MAA |
| | Stage 2 (65%): 14.1 BA/85.7 MMA/0.2 MAA |
| P5 | Stage 1 (35%): 11.2 BA/83.5 MMA/5.1 PEM/0.2 MAA |
| | Stage 2 (65%): 14.1 BA/85.7 MMA/0.2 MAA |
| P6 | Stage 1 (35%): 11 BA/82.2 MMA/6.6 PEM/0.2 MAA// 0.1 ALMA |
| | Stage 2 (65%): 14.1 BA/85.7 MMA/0.2 MAA//0.1 ALMA |
| P7 | Stage 1 (35%): 11 BA/82 MMA/6.6 PEM/0.2 MAA//ALMA |
| | Stage 2 (65%): 14.1 BA/85.7 MMA/0.2 MAA//0.2 ALMA |

MMA = methyl methacrylate
MAA = methacrylic acid
BA = butyl acrylate
PEM = phosphoethyl methacrylate
ALMA = allyl methacrylate For polymer P1, a Stage 1 monomer emulsion was prepared by mixing 65.5 g DI water, 16.5 g (30% active) anionic surfactant-A (surfactant having an average composition of lauryl-(ethylene oxide)$_4$ sodium sulfate; 30 wt % solids), 27.14 g BA, 202.36 g MMA, 0.50 g MAA, and 16.2 g PEM. A Stage 2 monomer emulsion was then prepared by mixing 136 g DI water, 15.4 g (30% active) anionic surfactant A, 64.5 g BA, 392.2 g MMA, and 0.95 g MAA. A 3 liter reactor, four-necked round bottom flask equipped with a paddle stirrer, a thermocouple, nitrogen inlet, and reflux condenser was assembled. To the flask was added 1,170 g DI water and 16.5 g (30% active) anionic surfactant A, and stirring was started. The contents of the flask were heated to 84° C. under a nitrogen atmosphere. A solution of 1.4 g NaPS in 13 g DI water was added. The stage 1 monomer emulsion was fed into the reactor over 40 minutes. A solution of 0.71 g NaPS in 43 g DI water was fed separately to the flask for 40 minutes. After the addition of Stage 1 monomer emulsion the container was rinsed with a small portion of DI water and added into the flask. The NaPS co-feed was stopped and the reaction held at 87° C. for 10 minutes. The Stage 2 monomer emulsion was fed into the flask over 65 minutes. The NaPS co-feed was re-started and fed for 65 minutes. Furthermore, a separate solution containing 5.3 g of ammonium hydroxide (28% solution), 20 g of water was fed over 65 minutes. After the addition of Stage 2 monomer emulsion the container was rinsed with a small portion of DI water and fed into the flask. The contents of the flask were maintained at 84-86° C. for 5 minutes. The batch was then cooled to 65° C. A redox pair of hydrogen peroxide aqueous solution and iso-ascorbic acid solution was fed into the kettle separately. The batch was cooled to room temperature.

Polymers P2-P7 were prepared substantially as described above, with the appropriate changes in monomer amounts as recited in Table 1.

Example 2

Preparation of Comparative Copolymer Particles

Comparative copolymer particles contain the components recited in Table 2.

TABLE 2

Comparative Copolymer Particles

| Sample | Monomer (wt %) |
|---|---|
| PA | Stage 1 (35%): 11.8 BA/88 MMA/0.2 MAA<br>Stage 2 (65%): 14.1 BA/85.7 MMA/0.2 MAA |

MMA = methyl methacrylate
MAA = methacrylic acid
BA = butyl acrylate

For polymer PA, a Stage 1 monomer emulsion was prepared by mixing 65.5 g DI water, 16.5 g (30% active) anionic surfactant-A (surfactant having an average composition of lauryl-(ethylene oxide)$_4$ sodium sulfate; 30 wt % solids), 27.14 g BA, 202.36 g MMA, and 0.50 g MAA. A Stage 2 monomer emulsion was prepared by mixing 136 g DI water, 15.4 g (30% active) anionic surfactant A, 64.5 g BA, 392.2 g MMA, and 0.95 g MAA. A 3 liter reactor, four-necked round bottom flask equipped with a paddle stirrer, a thermocouple, nitrogen inlet, and reflux condenser was assembled. To the flask was added 1,170 g DI water and 16.5 g (30% active) anionic surfactant A, and stirring was started. The contents of the flask were heated to 84° C. under a nitrogen atmosphere. A solution of 1.4 g NaPS in 13 g DI water was added. The stage 1 monomer emulsion was fed into the reactor over 40 minutes. A solution of 0.71 g NaPS in 43 g DI water was fed separately to the flask for 40 minutes. After the addition of Stage 1 monomer emulsion the container was rinsed with a small portion of DI water and added into the flask. The NaPS co-feed was stopped and the reaction held at 87° C. for 10 minutes. The Stage 2 monomer emulsion was fed into the flask over 65 minutes. The NaPS co-feed was re-started and fed for 65 minutes. Furthermore, a separate solution containing 5.3 g of ammonium hydroxide (28% solution), 20 g of water was fed over 65 minutes. After the addition of Stage 2 monomer emulsion the container was rinsed with a small portion of DI water and fed into the flask. The contents of the flask were maintained at 84-86° C. for 5 minutes. The batch was then cooled to 65° C. A redox pair of hydrogen peroxide aqueous solution and iso-ascorbic acid solution was fed into the kettle separately. The batch was cooled to room temperature.

Example 3

Characterization of Exemplary and Comparative Copolymer Particles

Copolymer particles as prepared in Examples 1 and 2 above were evaluated for pH, % solids, and particle size, as show in Table 3.

TABLE 3

Characterization of Copolymer Particles

| Sample | $T_g$ (° C.) | pH | % Solids | Particle Size (nm) |
|---|---|---|---|---|
| P1 | 87.01 | 7.57 | 30.17 | 61.7 |
| P2 | 86.03 | 8.64 | 30.37 | 58.6 |
| P3 | 86.40 | 9.45 | 29.99 | 61.2 |
| P4 | — | — | 29.76 | 110 |
| P5 | 87.69 | — | 29.91 | 132 |
| P6 | 86.86 | 8.78 | 31.64 | 47.4 |
| P7 | 86.54 | 8.32 | 31.27 | 53.9 |
| PA | 85.46 | 8.88 | 29.95 | 56.1 |

The $T_g$ was measured by DSC using a TA Instruments Q2000 DSC. The particle size was measured using a Matex CHDF 2000.

Example 4

Preparation of Sunscreen Formulations Using a Hydrophilic Dispersion

Exemplary sunscreen compositions according to the present invention, and a comparative sunscreen formulation, contain the components recited in Table 4.

TABLE 4

Sunscreen Formulations Using Hydrophilic Dispersion

| Trade Name | INCI | Control (wt %) | E1 (wt %) | E2 (wt %) | E3 (wt %) | E4 (wt %) | E5 (wt %) | CA (wt %) |
|---|---|---|---|---|---|---|---|---|
| Phase A | | | | | | | | |
| DI Water | — | 75.89 | 59.48 | 59.48 | 59.48 | 59.48 | 59.48 | 59.48 |
| EDTA | Ethylenediaminetetraacetic acid tetrasodium salt | 0.05 | 0.05 | 0.05 | 0.05 | 0.05 | 0.05 | 0.05 |
| Keltrol CGT | Xanthan Gum | 0.5 | 0.5 | 0.5 | 0.5 | 0.5 | 0.5 | 0.5 |
| 1,2 Propanediol | Propylene Glycol | 1 | 1 | 1 | 1 | 1 | 1 | 1 |
| Glucam E-10 | Methyl Gluceth-10 | 1 | 1 | 1 | 1 | 1 | 1 | 1 |

TABLE 4-continued

Sunscreen Formulations Using Hydrophilic Dispersion

| Trade Name | INCI | Control (wt %) | E1 (wt %) | E2 (wt %) | E3 (wt %) | E4 (wt %) | E5 (wt %) | CA (wt %) |
|---|---|---|---|---|---|---|---|---|
| Phase B | | | | | | | | |
| Lipopeg 39-S[1] | PEG 40 Stearate | 1 | 1 | 1 | 1 | 1 | 1 | 1 |
| Tegin M[2] | Glyceryl Stearate | 1 | 1 | 1 | 1 | 1 | 1 | 1 |
| Promulgen D[3] | Cetearyl Alcohol (and) Ceteareth-20 | 3 | 3 | 3 | 3 | 3 | 3 | 3 |
| Finsolv TN[4] | C12-15 Alkyl Benzoate | 3.5 | 3.5 | 3.5 | 3.5 | 3.5 | 3.5 | 3.5 |
| XIAMETER® PMX-200 Silicone Fluid 100 CS[5] | Dimethicone DC 200 Fluid (100 cs) | 2 | 2 | 2 | 2 | 2 | 2 | 2 |
| Phase C | | | | | | | | |
| $TiO_2$ Hydrophilic Dispersion (40-50%)[6] | Water (and) $TiO_2$ (and) Butylene Glycol (and) Silica (and) Glycerin | 10 | 10 | 10 | 10 | 10 | 10 | 10 |
| P1 | — | — | 16.57 | — | — | — | — | — |
| P2 | — | — | — | 16.57 | — | — | — | — |
| P3 | — | — | — | — | 16.57 | — | — | — |
| P4 | — | — | — | — | — | 16.57 | — | — |
| P5 | — | — | — | — | — | — | 16.57 | — |
| PA | — | — | — | — | — | — | — | 16.57 |
| Phase D | | | | | | | | |
| Optiphen[7] | Phenoxyethanol (and) Caprylyl Glycol | 0.9 | 0.9 | 0.9 | 0.9 | 0.9 | 0.9 | 0.9 |
| Total | | 100 | 100 | 100 | 100 | 100 | 100 | 100 |

[1] Available from Lipo Chemical
[2] Available from Degussa
[3] Available from Croda
[4] Available from Finetex
[5] Available from Dow Corning
[6] Available from Kobo Products under trade name WBG45M40ML
[7] Available from International Specialty Products (ISP)

The sunscreen formulations were prepared by mixing all Phase A components into a container and heating to 75° C. Phase B was mixed separately and heated to 75° C. to ensure that all fatty components were dissolved. Phase A and Phase B were combined while mixing at variable speeds of 800-1,000 rpm for 15-20 minutes. The resulting mixture was then cooled to 55-60° C. and Phase C was added into the batch while mixing at variable speeds of 800-1,000 rpm for 15-20 minutes. Once the temperature reached below 45° C., Phase D was added into the batch while mixing at variable speeds of 800-1,000 rpm until cooled to room temperature.

Example 5

Preparation of Sunscreen Formulations Using a $TiO_2$ Powder

Exemplary sunscreen compositions according to the present invention, and a comparative sunscreen formulation, contain the components recited in Table 5.

TABLE 5

Sunscreen Formulations Using TiO$_2$ Powder

| Trade Name | INCI | Control (wt %) | E6 (wt %) | E7 (wt %) | E8 (wt %) | E9 (wt %) | E10 (wt %) | CB (wt %) |
|---|---|---|---|---|---|---|---|---|
| Phase A | | | | | | | | |
| DI Water | — | 75.89 | 59.48 | 59.48 | 59.48 | 59.48 | 59.48 | 59.48 |
| EDTA | Ethylenediaminetetraacetic acid tetrasodium salt | 0.05 | 0.05 | 0.05 | 0.05 | 0.05 | 0.05 | 0.05 |
| Keltrol CGT | Xanthan Gum | 0.5 | 0.5 | 0.5 | 0.5 | 0.5 | 0.5 | 0.5 |
| 1,2 Propanediol | Propylene Glycol | 1 | 1 | 1 | 1 | 1 | 1 | 1 |
| Glucam E-10 | Methyl Gluceth-10 | 1 | 1 | 1 | 1 | 1 | 1 | 1 |
| Phase B | | | | | | | | |
| Lipopeg 39-S[1] | PEG 40 Stearate | 1 | 1 | 1 | 1 | 1 | 1 | 1 |
| Tegin M[2] | Glyceryl Stearate | 1 | 1 | 1 | 1 | 1 | 1 | 1 |
| Promulgen D[3] | Cetearyl Alcohol (and) Ceteareth-20 | 3 | 3 | 3 | 3 | 3 | 3 | 3 |
| Finsolv TN[4] | C12-15 Alkyl Benzoate | 3.5 | 3.5 | 3.5 | 3.5 | 3.5 | 3.5 | 3.5 |
| XIAMETER ® PMX-200 Silicone Fluid 100 CS[5] | Dimethicone DC 200 Fluid (100 cs) | 2 | 2 | 2 | 2 | 2 | 2 | 2 |
| Phase C | | | | | | | | |
| TiO$_2$ Hydrophilic Powder | TiO2 (and) Alumina (and) Silica | 10 | 10 | 10 | 10 | 10 | 10 | 10 |
| P1 | — | — | 16.57 | — | — | — | — | — |
| P2 | — | — | — | 16.57 | — | — | — | — |
| P3 | — | — | — | — | 16.57 | — | — | — |
| P4 | — | — | — | — | — | 16.57 | — | — |
| P5 | — | — | — | — | — | — | 16.57 | — |
| PA | — | — | — | — | — | — | — | 16.57 |
| Phase D | | | | | | | | |
| Optiphen[7] | Phenoxyethanol (and) Caprylyl Glycol | 0.9 | 0.9 | 0.9 | 0.9 | 0.9 | 0.9 | 0.9 |
| Total | | 100 | 100 | 100 | 100 | 100 | 100 | 100 |

[1] Available from Lipo Chemical
[2] Available from Degussa
[3] Available from Croda
[4] Available from Finetex
[5] Available from Dow Corning
[6] Available from Kobo Products under trade name TA-100.
[7] Available from International Specialty Products (ISP)

The sunscreen formulations were prepared by mixing all Phase A components into a container and heating to 75° C. Phase B was mixed separately and heated to 75° C. to ensure that all fatty components were dissolved. Phase A and Phase B were combined while mixing at variable speeds of 800-1,000 rpm for 15-20 minutes. The resulting mixture was then cooled to 55-60° C. and Phase C was added into the batch while mixing at variable speeds of 800-1,000 rpm for 15-20 minutes. Once the temperature reached below 45° C., Phase D was added into the batch while mixing at variable speeds of 800-1,000 rpm until cooled to room temperature.

Example 6

SPF Boost Study of Sunscreen Formulations Prepared with Hydrophilic Dispersion

The SPF value of the formulations as prepared in Example 4 were measured using an in vitro technique substantially according to the following protocol in compliance with the COLIPA 2007 method:

Initially, the weight of a roughened PMMA substrate (purchased from SCHÖNBERG GmbH & Co. KG, Hamburg/Germany) is measured. The batch to be tested is then deposited on the substrate and then quickly leveled with a 7 micron draw down bar to achieve a thin, uniform layer. The layer is allowed to dry for about 20 minutes, and the weight of the substrate plus dry uniform layer is determined. The UV absorption of dry uniform layer is measured using a LABSPHERE UV-2000S spectrometer at multiple points on the layer.

The percent solids of the layer is measured using an OHAUS MB45 solids analyzer. Using the weight of the dry film, and the solids content of the layer, the weight, and consequently the density of the original wet layer immediately after deposition can be calculated. Using this information, the SPF can be calculated by the following equation:

$$SPF = \frac{\int_{290nm}^{400nm} E(\lambda)S(\lambda)\partial\lambda}{\int_{290nm}^{400nm} E(\lambda)S(\lambda)10^{(-A(\lambda))}\partial\lambda}$$

Where $E(\lambda)$=spectral irradiance of the Standard Sun Spectrum; $S(\lambda)$=erythemal action spectrum at wavelength $\lambda$; and $A(\lambda)$=corrected spectral absorbance at wavelength $\lambda$ (a correction factor is calculated to extrapolate the data to establish what the absorbance would be at a wet layer density of 2.0 mg/cm$^2$ (using the original wet layer immediately after deposition).

The results of the SPF measurements are shown in Table 6 as percent SPF improvement from a composition with no copolymer particles having an SPF of 15.51.

TABLE 6

SPF Performance of Hydrophilic Dispersion Sunscreen Formulations

| Formulation | SPF Boost (%) |
| --- | --- |
| CA | 82.78 |
| E1 | 163 |
| E2 | 139.45 |
| E3 | 185.94 |

The results demonstrate that exemplary sunscreen formulations prepared in accordance with the present invention provide a SPF boost value significantly higher than comparative formulations.

Example 7

SPF Boost Study of Sunscreen Formulations Prepared with Hydrophilic Powder

The SPF value of the formulations as prepared in Example 5 were measured using an in vitro technique substantially according to the protocol described in Example 6. The results of the SPF measurements are shown in Table 7 as percent SPF improvement from a composition with no copolymer particles having an SPF of 11.

TABLE 7

SPF Performance of Hydrophilic Powder Sunscreen Formulations

| Formulation | SPF Boost (%) |
| --- | --- |
| CB | X* |
| E6 | 172 |
| E7 | 131 |

The results demonstrate that exemplary sunscreen formulations prepared in accordance with the present invention provide a SPF boost significantly higher than comparative formulations.

Example 8

Film Property Study of Sunscreen Formulations Prepared with Hydrophilic Dispersion The quality of films cast from formulations as prepared in Example 4 was assessed on a PMMA plate. The plate was placed on a vacuum drawdown board, and a bead of the formulation was deposited across the plate in front of a rod (wire round Rod #7). The rod was then used to pull the formulation across the substrate. The plate was then dried for about 1 hour under ambient conditions at room temperature (20-25° C.). The films were evaluated and given ratings of "Poor" (cracking/flocculated particles), "Good" (minimal flocculation/even dispersion), and "Very Good" (no flocculation/smooth film). The results of the film quality study are shown in Table 8.

TABLE 8

Film Quality of Sunscreen Formulations Prepared with Hydrophilic Dispersion

| Formulation | Film Rating |
| --- | --- |
| CA | Poor |
| E1 | Very Good |
| E2 | Very Good |
| E3 | Very Good |
| E4 | Very Good |
| E5 | Very Good |

*No polymer film formed.

The results demonstrate that exemplary sunscreen formulations prepared in accordance with the present invention provide a film quality significantly better than comparative formulations.

Example 9

Film Property Study of Sunscreen Formulations Prepared with Hydrophobic Powder

The quality of films cast from formulations as prepared in Example 5 was assessed on a PMMA plate using the procedure described in Example 8. The results of the film quality study are shown in Table 9.

TABLE 9

Film Quality of Sunscreen Formulations Prepared with Hydrophilic Powder

| Formulation | Film Rating |
| --- | --- |
| CB | Poor |
| E6 | Very Good |
| E7 | Very Good |
| E8 | Very Good |
| E9 | Very Good |
| E10 | Very Good |

The results demonstrate that exemplary sunscreen formulations prepared in accordance with the present invention provide a film quality significantly better than comparative formulations.

What is claimed is:

1. A skin care composition comprising:
(a) 0.1 to 20 weight % inorganic metal oxide particles, based on the weight of the composition, wherein the inorganic metal oxide particles are transparent zinc oxide, transparent titanium dioxide or mixtures thereof;
(b) 0.1 to 15 weight % copolymer particles dispersed in an aqueous medium, based on the weight of the composition, wherein the copolymer particles comprise polymerized units derived from (i) 0.1 to 20 weight % of phosphorus acid monomers selected from the group consisting of 2-phosphoethyl (meth)acrylate, 2-phosphopropyl (meth)acrylate, 3-phosphopropyl (meth)acrylate and 3-phospho-2-hydroxypropyl (meth)acrylate, and (ii) 80 to 99.9 weight % of comonomers selected from the group consisting of styrene, butadiene, α-methyl styrene, vinyl toluene, vinyl naphthalene, ethylene, propylene, vinyl acetate, vinyl versatate, vinyl chloride, vinylidene chloride, acrylonitrile, methacrylonitrile, (meth)acrylamide, esters of (meth)acrylic acid, other (meth)acrylates and carboxylic acid containing monomers; wherein the comonomers comprise at least one of butyl acrylate, methyl methacrylate, and methacrylic acid; and wherein the copolymer particles comprise no more than 1 weight % polymerized units of crosslinker;
(c) a dermatologically acceptable carrier and
(d) a sunscreen active selected from the group consisting of para aminobenzoic acid, avobenzone, cinoxate, dioxybenzone, homosalate, menthyl anthranilate, octocrylene, octyl methoxycinnamate, octyl salicylate, oxybenzone, padimate O, phenylbenzimidazole sulfonic acid, sulisobenzone, trolamine salicylate, benzophenones, benzylidenes, salicylates, diethanolamine methoxycinnamate, digalloyl trioleate, ethyl dihydroxylpropyl PABA, glyceryl aminobenzoate and lawsone with dihydroxy acetone and red petrolatum;
wherein the skin care composition includes the inorganic metal oxide particles and the copolymer particles in a weight ratio of 2:8 to 8:2;
wherein the copolymer particles are adsorbed onto the surface of the inorganic metal oxide particles; and
wherein the skin care composition has improved absorbance of UV radiation and increased SPF performance compared with a composition containing an equivalent level of the inorganic metal oxide particles in the absence of the copolymer particles.

2. The skin care composition of claim 1, wherein the phosphorus acid monomers comprise 2-phosphoethyl (meth)acrylate.

3. The skin care composition of claim 1, wherein the comonomers comprise butyl acrylate, methyl methacrylate, and methacrylic acid.

4. The skin care composition of claim 1, wherein the copolymer particles are formed in a single stage reaction.

5. The skin care composition of claim 1, wherein the copolymer particles are formed in a two stage reaction.

6. The skin care composition of claim 1, wherein the copolymer particles comprise polymerized units derived from (i) 0.5 to 10 weight % of the phosphorus acid monomers and (ii) 90 to 99.5 weight % of the comonomers.

7. The skin care composition of claim 1, wherein the copolymer particles comprise polymerized units derived from (i) 1 to 6 weight % of the phosphorus acid monomers and (ii) 94 to 99 weight % of the comonomers.

8. The skin care composition of claim 1, wherein the skin care composition comprises (a) 0.5 to 18 weight % of the inorganic metal oxide particles and (b) 0.5 to 10 weight % of the copolymer particles.

9. The skin care composition of claim 1, wherein the skin care composition comprises (a) 1 to 15 weight % of the inorganic metal oxide particles and (b) 1 to 6 weight % of the copolymer particles.

10. The skin care composition of claim 2, wherein the copolymer particles comprise butyl acrylate, methyl methacrylate and methacrylic acid.

11. The skin care composition of claim 10, wherein the copolymer particles comprise polymerized units derived from (i) 0.5 to 10 weight % of the phosphorus acid monomers and (ii) 90 to 99.5 weight % of the comonomers.

12. The skin care composition of claim 10, wherein the copolymer particles comprise polymerized units derived from (i) 1 to 6 weight % of the phosphorus acid monomers and (ii) 94 to 99 weight % of the comonomers.

13. The skin care composition of claim 11, wherein the skin care composition comprises (a) 0.5 to 18 weight % of the inorganic metal oxide particles and (b) 0.5 to 10 weight % of the copolymer particles.

14. The skin care composition of claim 11, wherein the skin care composition comprises (a) 1 to 15 weight % of the inorganic metal oxide particles and (b) 1 to 6 weight % of the copolymer particles.

15. The skin care composition of claim 12, wherein the skin care composition comprises (a) 0.5 to 18 weight % of the inorganic metal oxide particles and (b) 0.5 to 10 weight % of the copolymer particles.

16. The skin care composition of claim 12, wherein the skin care composition comprises (a) 1 to 15 weight % of the inorganic metal oxide particles and (b) 1 to 6 weight % of the copolymer particles.

17. A method of protecting skin from UVA and UVB damage comprising topically administering to the skin a sunscreen composition according to claim 1.

* * * * *